US006027893A

United States Patent [19]
Ørum et al.

[11] Patent Number: 6,027,893
[45] Date of Patent: Feb. 22, 2000

[54] METHOD OF IDENTIFYING A NUCLEIC ACID USING TRIPLE HELIX FORMATION OF ADJACENTLY ANNEALED PROBES

[75] Inventors: Henrik Ørum, Vorlose; Michael Naesby, Valby, both of Denmark

[73] Assignee: Roche Diagnostics GmbH, Mannheim, Germany

[21] Appl. No.: 08/993,140

[22] Filed: Dec. 18, 1997

[30] Foreign Application Priority Data

Dec. 21, 1996 [WO] WIPO .................................. 96120710

[51] Int. Cl.[7] .............................. C12Q 1/68; C12P 19/34; C07H 21/00
[52] U.S. Cl. ............................ 435/6; 435/91.1; 536/29.3; 536/24.31; 536/24.32
[58] Field of Search ...................... 435/6, 91.1; 536/24.3, 536/24.31, 24.32, 24.33

[56] References Cited

FOREIGN PATENT DOCUMENTS 0 552 931 A1   7/1993   European Pat. Off. .

OTHER PUBLICATIONS

Orum et al. Biotechniques vol. 19, No. 3, 1995.
International Publication No. WO 92/11390 published Jul. 9, 1992.
International Publication No. WO 93/06240 published Apr. 1, 1993.
International Publication No. WO 95/08556 published Mar. 30, 1995.
International Publication No. WO 95/14706 published Jun. 1, 1995.

*Primary Examiner*—Kenneth R. Horlick
*Assistant Examiner*—Jeffrey Siew
*Attorney, Agent, or Firm*—Nikaido Marmelstein Murray & Oram, LLP.

[57] ABSTRACT

A method for determining a nucleic acid A, comprising the formation of a complex, including two molecules capable of hybridizing to A and of participating in formation of a triplex structure with an additional nucleic acid or nucleic acid analogue is useful for sensitive and specific determination.

24 Claims, 4 Drawing Sheets

Lane 1: D

Lane 2: B + D

Lane 3: C + D

Lane 4: B + C + D

Lane 5: A + B + D

Lane 6: A + C + D

Lane 7: A + B + C + D

Lane 8: A + B + C

Lane 9: A + B

Lane 10: A + C

Lane 11: A

SEQUENCE LISTING

```
<160> NUMBER OF SEQ ID NOS: 2

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      Oligodeoxyribonucleotide

<400> SEQUENCE: 1
aaagacaatg gattacctat aactgtagac tcggcttggg                              40

<210> SEQ ID NO 2
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      Oligodeoxyribonucleotide

<400> SEQUENCE: 2
tagttgtgac gtacagaagg agaa                                              24
```

METHOD OF IDENTIFYING A NUCLEIC ACID USING TRIPLE HELIX FORMATION OF ADJACENTLY ANNEALED PROBES

FIELD OF THE INVENTION

The present invention relates to a method of identifying a nucleic acid using at least two, adjacently annealed probes capable of participating in the formation of a triple helix structure and compositions of matter containing the nucleic acid and said probes and compositions of matter containing the nucleic acid, and said probes as well as a third probe.

BACKGROUND OF THE INVENTION

Detection and quantification of nucleic acid molecules constitutes a fundamental element in several diagnostic techniques. An essential feature of such techniques is the ability of probes (a nucleic acid or nucleic acid analogue) to hybridize specifically to a complementary nucleic acid sequence. For hybridisation to occur some standard conditions have to be met regarding e.g. salt concentration and temperature, but the major determining factor is the number of fully matched nucleobases in the hybrid of two hybridizing strands. In hybrids of relatively short length, e.g. 6–10 basepairs, a single base pair mismatch will result in a drastic decrease in thermal stability, whereas the relative reduction of stability caused by a single base pair mismatch (or a deletion/insertion) becomes increasingly less with increasing length of the hybrid.

For diagnostic purposes, it is often desirable to identify a sequence of nucleobases which is present only in the gene or in the organism in question, but absent in any background nucleic acid that may be present in the sample. For any given sequence of nucleobases to be statistically unique in a typical sample, like the human genome, the length of the sequence will have to be in the order of 18–20 bases, which on the other hand will enhance its capacity to accomodate mismatches, without any major loss of thermal stability. Thus, smaller probes may have the disadvantage of not being statistically unique, whereas longer probes may have the disadvantage of not being able to discriminate mismatches because the overall stability of the hybrid is not significantly affected.

SUMMARY OF THE INVENTION

The present invention describes a way of circumventing this problem, by combining the property of small sequences of superior discrimination of mismatches with the statistical specificity of longer nucleobase sequences. The invention uses two different nucleic acid analogues hybridizing to relatively short target sequences adjacently located on the nucleic acid to be identified. Each of the two probes, in addition to the sequence binding to the target nucleic acid, contains a second nucleobase sequence capable of forming a triple helix structure together with a complementary nucleic acid or nucleic acid analogue. Triple helix formation is greatly enhanced when the two probes are correctly bound, i.e. adjacently to each other, and the complex formed indirectly evidences the presence of the combined target site on the nucleic acid to be identified.

Subject of the present invention is a method of identifying a nucleic acid A, having a sequence A1 and a sequence A2 adjacently connected, containing contacting the nucleic acid with a first nucleic acid analogue B, having a sequence B1 complementary to sequence A1 and a sequence B2 capable of participating in a triple helix structure (preferably containing a complementary nucleic acid), a second nucleic acid analogue C, having a sequence C1 capable of participating in a triple helix structure (and preferably a sequence C2 complementary to sequence A2) and further preferred yet another nucleic acid or nucleic acid analogue D (having a sequence D1, capable of triple helix formation together with sequences B2 and C1, and a segment D2, containing either an additional nucleobase sequence available for hybridization or any kind of label known in the art), and determining the formation of a complex containing the nucleic acid A, the analogues B and C, and preferably a nucleic acid or nucleic acid analogue D. A further subject are intermediate products in this complex formation, or possible preformed probe compounds, as well as a kit of reagents for use in the method of the invention.

DETAILED DESCRIPTION OF THE INVENTION

Figure 1:
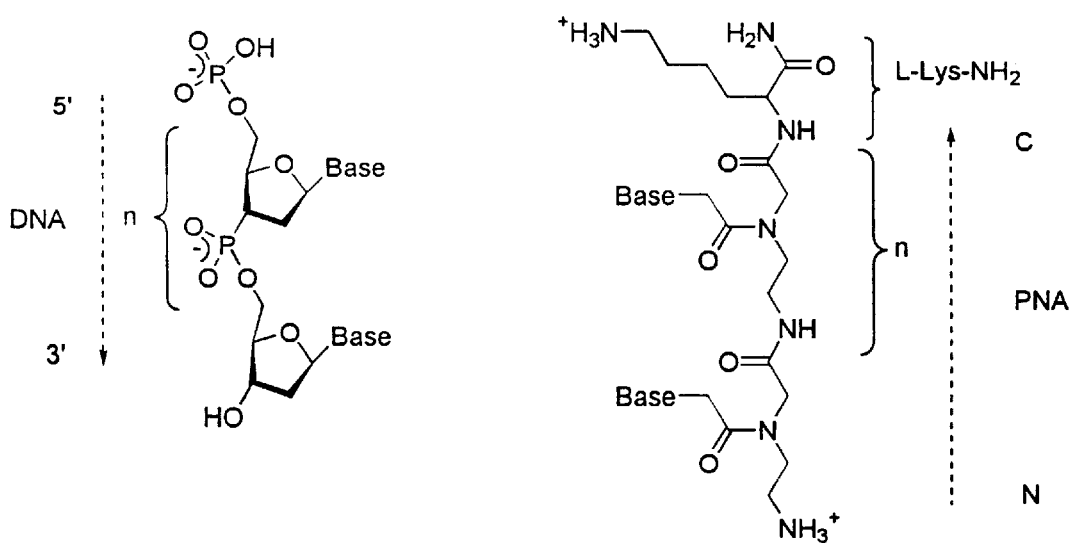
FIG. 1 shows schematically the structure of an exemplified peptide nucleic acid (PNA) while bound to DNA in the preferred antiparallel mode.

At least one segment of each of the components of the complexes formed in the present invention is defined by, and has, a nucleobase sequence. The sequence can be specific or unspecific, determined by the use of the segment or component in the method of the invention. Nucleobases can be natural nucleobases, like A, C, G, T and U, or non-natural bases, like 7-deaza-G, or mixtures thereof The term "nucleic acid analogue" means that the molecule contains a backbone of non-natural origin and structure. Besides non-natural backbone, parts of the nucleic acid analogue can in addition contain a backbone made up of natural nucleic acid backbones, i.e. sugar phosphate moieties. The preferred case is that the nucleic acid analogue contains a backbone not containing sugar phosphate moieties as in natural nucleic acids.

A nucleic acid A can be any molecule containing two sequences of nucleobases, each of which are at least 5 bases long. The nucleobases are preferably covalently linked to a backbone, in a linear manner such that the molecule can bind by base pairing to a nucleic acid or nucleic acid analogue containing a sequence of bases complementary to the sequence of bases contained in molecule A. Examples of molecules A are nucleic acids, like RNA, DNA, or derivatives thereof, and nucleic acid analogues. Molecule A can further include additional molecular moieties, for example any kind of label.

An essential feature of nucleic acid A is that it has a sequence A1 and a sequence A2 adjacently connected.

Usually sequence A1 is an integral part of the nucleic acid A to be determined and can therefore not be altered. According to the invention a sequence B1 of nucleic acid analogue B (which will be described later) will be chosen such that it is complementary to sequence A1, because sequence A1 cannot be altered, and sequence A1 is, thus, defined by a specific relationship to sequence B1 of nucleic acid analogue B. Sequence A2 is similarly defined by its relationship to sequence C2 of nucleic acid analogue C. Usually sequence C2 will be chosen such that it is complementary to sequence A2, because sequence A2 cannot be altered. For the identification of a nucleic acid, according to the present invention, sequences A1 and A2 are selected such that they have the required specificity for unambiguous identification. The sequences A1 and A2 are located on the same strand of nucleic acid A. The specificity will depend upon the circumstances of the determination. If a very specific nucleic acid A needs to be determined in a sample containing no other nucleic acid but other biological components, like e.g. proteins, there is no need for extentive search for appropriate sequences A1 and A2. If, however, there are more different nucleic acid species in the sample, sequences A1 and A2 should be selected such that they are not found adjacent to each other on any nucleic acid other than A. Most preferably none of the sequences A1 and A2 should occur on any nucleic acid other than A. In a preferred embodiment, there are from 0 to 5 nucleobases on the strand between sequence A1 and sequence A2 on nucleic acid A. Most preferably there are none or only a single nucleobase between A1 and A2. The sequences A1 and A2 may have the same length or may be different in length, and are each, preferably, between 6 and 15, bases long.

The origin and function of the nucleic acid A (also called analyte nucleic acid) will be defined by the purpose of the determination. It may be the nucleic acid of a particular infectious agent, like a virus or bacterium, or may be part of a genome, in which a sequence is to be confirmed, e.g. for determining predisposition for diseases like cancer or hereditary genetic diseases. The nucleic acid may have been subject of a prior preparation step, including purification, isolation or amplification. Preferably the nucleic acid have been separated from cellular debris, and a specific or unspecific part of the nucleic acid may have been amplified, for example by culture or by the polymerase chain reaction (PCR). It may be a molecule originating from a sample, in which the presence and/or amount of this molecule is intended to be determined and analyzed, or it may itself be a probe or probe unit, intended to be used for the determination of another analyte. Further, the amount of A may be unknown, for example in methods for determining A as an analyte in a sample, or it can be known, for example if a defined amount of A has been added to a sample as part of an effort to determine a secondary analyte (e.g. proteins, antibodies, haptens etc.) different from A.

The first nucleic acid analogue B is defined to contain a sequence B1 complementary to sequence A1 and a sequence B2, capable of participating in a triple helix structure containing a complementary nucleic acid. Thus, the nucleobase sequence B1 is chosen such that it is complementary to sequence A1 of nucleic acid A, and the specific choice of sequence will depend upon the specificity needed for the determination of the nucleic acid. In some cases a sequence which is 100% identical to A1 will not be required, e.g. if the discrimination against other nucleic acids is not required. However, in accordance with the present invention, complementarity means at least 60%, more preferrable 80% and most preferrable at least 90% identical nucleobase sequence of two strands. Most preferably sequence B1 is chosen such that it binds to A1 via double helix formation, and not via triple helix formation. Usually sequence B1 will contain all four natural nucleobases, and sequence B1 may contain a natural backbone. However, it is preferred that sequence B1 contains a backbone having a higher affinity to nucleic acid A than the corresponding sequence with a natural backbone, and preferably B1 consists of a peptide nucleic acid. Sequence B2 must be capable of participating in a triple helix structure containing a complementary nucleic acid. Therefore, only nucleobases which are able to participate in triple helix structures are allowed to be included within this sequence. Sequence C1 must be chosen accordingly in sequence and nature.

The invention further requires a second nucleic acid analogue C having a sequence C1 and a sequence C2. Analogue C differs from analogue B in that its sequence C2 must bind to a different part of nucleic acid A, namely to the sequence A2. Sequence C2 is, therefore, chosen to be complementary to sequence A2. Most preferable sequence A1 and sequence A2 do not overlap on nucleic acid A but are adjacent to each other as defined above. Again, sequence C2 is preferably a peptide nucleic acid like sequence B1. The sequence of C1 is chosen such that it is capable of participating in a triple helix structure containing a complementary nucleic acid. Preferably C1 has a sequence being at least 60%, preferably 80% and, most preferable, 90% identical to contiguous bases on sequence B2. The sequences C1 and B2 may have a length of between 5 and 30, preferably between 6 and 20 bases. Parts B1 and B2 as well as C1 and C2 can be connected directly or may be separated by a specific number of bases, or a specific distance, which could include any linker or spacer not interfering with the formation of the desired complex. Especially when there is a distance of more than zero bases between A1 and A2 it may be appropriate to include a linking moiety between B1 and B2, and C1 and C2, respectively.

A nucleic acid or nucleic acid analogue D contains a sequence D1 which can participate in a triple helix structure containing sequences B2 and C1 of the first and second nucleic acid analogues. This sequence, intended for triple helix structure formation, will, therefore, be designed such that it contains bases capable of forming both Watson Crick and Hoogsteen base pairings with B2 and C1. The conditions for triplex formation are described elsewhere. In addition, D may contain other parts (referred to as segment D2), not participating in triple helix structure formation. This can be an additional nucleobase sequence available for binding of secondary probes or it can, for example, be any detectable or immobilizable label moiety, such as digoxigenin, biotin, fluorescein or ruthenium bispyridine complexes. These moieties can either be detected directly or can be made visible by further reaction with compounds, e.g. enzyme-linked antibodies, suitable for detection. Alternatively, the label can be used for the capture, either of D itself, nor of any complex including D, on a solid support. In a special example D may even be covalently linked to a solid support.

According to the invention a probe is an entity used for binding a label of any kind to a molecule to be determined. This binding may be direct or indirect. The use of probe molecules like B, C, and D containing only one kind of backbone throughout the whole molecule has the advantage of easy synthesis of these probe molecules. The molecules can be easily synthesized totally from monomeric units without the need of a subsequent linking step. On the other hand it may be desired to use a linker connecting two different segments, e.g. if the segments contain different backbones, or if segments are of opposing orientation It may then be advantageous to synthesize the segments independently and then connect them in a subsequent step.

The segments of nucleic acid analogues may be synthesized independently, especially if the segments contain different backbones. The synthesis of PNA is described in WO 92/20702, whereas the synthesis of ribo- and deoxyribonucleotides is possible according to a wide variety of methods, comprising chemical synthesis via phosporamidites or, especially for longer sequences, by methods including enzymes, like e.g. in the template dependent polymerase reaction. In a subsequent step the two segments are connected by a linker. The linker can include any molecular unit, such as amino acid residues, 8-amino-dioxa-octanoic acid (Ado, according to DE-A-3943522), or hexamethylen. Alternatively, if one of the groups at the termini is a phosphate group and that of another segment is an amino group, chimeras of such segments can be produced directly for example by the use of carbodilmides, such as EDC, in the presence of 1-hydroxybenzotriazol. In case of nucleic acid analogues containing a PNA and a DNA segment preferred linking methods connect hydroxyl groups of the DNA segment with one of the amino or carboxyl groups of the PNA segment (see FIG. 1). Molecules containing segments of nucleic acid and nucleic acid analogue are described in WO 95/08556 and WO 95/14706.

A triple helix structure, or triplex, is composed of three strands of molecules, each containing a nucleobase sequence capable of base pairing. Preferably the mode of binding between the three strands involves both Watson/Crick and Hoogsteen base pairing. The formation of triple helix structures usually requires a high degree of sequence complementarity of two of the strands involved to the third strand. In preferred triple helix structures two of the strands are composed of pyrimidine nucleobases while the third strand is composed of the corresponding purine nucleobases. Thus, each strand of the triple helical structure preferably has a length of at least six purine or six pyrimidine nucleobases, respectively. Each purine strand may be composed of either identical purine bases or a mixture of different purine bases, and similar variation is allowed within strands of pyrimidines.

It has been shown in WO 95/01370 that peptide nucleic acid (PNA) has the ability to form triplex structures with nucleic acids. Criteria for forming triple helices can therefore be taken from this patent application. PNA and its synthesis is disclosed in WO 92/20702 and WO 94/25477. In one embodiment the backbone of PNA is composed of repeating units of ethylaminoglycine moieties, where the nucleobases are bound to the glycine amino groups. PNA in this definition, therefore, contains an amino terminus ($NH_2$) and a carboxylic acid terminus (—COOH). These termini can be modified by the attachment of other moieties or by the omission of groups.

The present invention uses the formation of a complex between nucleic acid A, the first nucleic acid analogue B, and the second nucleic acid analogue C as a measure for the presence and/or the amount of nucleic acid A. In this complex, which is formed by base pairing between the three components, the components must bind in a specific, defined manner. For example, the orientation of segments B1 and C2, when bound to A, must be such that segments B2 and C1 are able to participate together in triple helix formation. This requirement for correct binding of the two probe moieties enhances the specificity of the determination. Further, it is required that sequences B2 and C1 do not directly base pair to nucleic acid A, and that sequences B1 and C2 do not base pair to each other or bind via triple helix formation to each other. The segments B1 and C2 are designed to bind to mutually exclusive segments A1 and A2 of molecule A, and the segments should not bind by base pairing to segments B2 and C1 of the same molecule (intramolecular binding). It is of some preference that none of the sequences of nucleic acid analogues B and C binds, to any substantial degree, to any other nucleic acids in the same sample.

The formation of triple helix, involving segments B2 and C1, can be determined using a nucleic acid or nucleic acid analogue D, capable of forming a triplex structure with B2 and C1. Thus, when bound indirectly to the nucleic acid A, D can be taken as a measure for the presence and/or amount of A. There are many ways to determine D, depending upon the molecular structure and composition. In addition to a segment D1, participating in triplex formation, D may contain a segment D2, which may contain either a nucleobase sequence or a tag for labelling or immobilizing the complex formed. The nucleic acid or nucleic acid analogue D can be added at any time to the reaction mixture, or to one of the reagents of the reaction.

In a first embodiment D is added to the reaction mixture from the start of the incubation of components A, B and C. The amount of D will be choosen such that it is in excess over the expected amount of complex formed between A, B and C.

In a second embodiment D is added to the reaction mixture after formation of a complex between nucleic acid A and the nucleic acid analogues B and C. While the formation of the complex between A, B and C will be performed under conditions favouring duplex formation, reaction with D will preferably be performed under conditions favouring, in addition, the formation of triple helix complexes.

The determination of the presence of D in the complex of A, B, C and D can be performed analogously to the methods known in the art for labels. The determination will preferably include calibration of the system by performing the identical reaction sequence for a reaction mixture containing known amounts of A.

Labels are generally known as moieties that are themselves immobilizable or detectable or can be immobilized/detected by coupling to additional moieties. Examples of labels are fluorescent moieties, (e.g. fluoresceine or rhodamine), enzymes, (e.g. peroxidase or phosphatase), immunologically active substances, like haptens, (e.g. digoxigenin), or protein binding tags (e.g. biotin) etc.

In one embodiment, determination of D is via one or more secondary probes, containing a sequence, complementary to a segment D2 of D, and a label. The secondary probes preferably do not contain a further nucleobase sequences complementary to other sequences contained in the reaction mixture.

In a second embodiment, determination of nucleic acid D is via direct labeling of D. In this embodiment segment D2 can itself be a detectable or inmmobilizable label. Thus, nucleic acid or nucleic analogue D acts as a probe participating directly, via segment D1, in the triple helix formation together with nucleic acid analogues B and C.

The determination of the complex ABCD can be made via yet another format embodiment. For example the mixture of the components, after incubation, may be subjected to electrophoresis. Thereby the complex formed can be separated from the starting compounds and discriminated by its differential migration characteristics. The spot containing the complex can be differentiated either by knowing the migration behaviour of the starting components or/and by independently determining the migration behaviour in a control setup where nucleic acid A is known to be present.

In another, more routine approach, either one of the components of the complex ABCD can be detectably labelled and another component immobilizably labelled. In this embodiment the conditions of hybridization must be controlled in such a way that all four components must be present for any complex formation to occur. This can be accomplished by selection of appropriate nucleobase sequences of each component, and/or by controlling the environment of the reaction, e.g. temperature, ionic strength etc.

The present invention generally makes use of the idea that the formation of triple helix structures allows the formation of strongly bound and highly specific structures. According to the invention it is possible to use a single, general sequence D1 for a number of different analyte nucleic acids A, detected by a common, general label contained within segment D2, or by either a general or a species specific secondary probe binding to segment D2. In the latter case the secondary probes will have different labels. Alternatively the sequence of D1 can be varied to allow detection of different analytes A, via complexes involving different probes B and C. This alternative can also be combined with either a general way of detection if only a single nucleic acid A is to be determined at a time, or with different ways of detection if more analyte nucleic acids are to be detected simultaneously. While the first approach will have the advantage that it is not necessary to synthesize probe D molecules of different sequences, the second approach may have the advantage of the possibility to better adapt the reaction to specific requirements. In the following an especially preferred embodiment will be described.

In a preferred mode of the invention a nucleic acid to be determined, now called the analyte nucleic acid, is preferably isolated in at least a crude preparation from a body fluid, for example urine, sputum, or blood, or fluids derived thereof (e.g. serum or plasma). If the nucleic acid is not readily accessible, for example if it is contained in a cell, some pre-preparational steps, for example the lysis of cell walls to release the nucleic acid, are performed. The nucleic acid to be determined, or part thereof, may then be amplified, for example using the PCR. An amplified segment of the analyte should contain the later used segments A1 and A2. If in vitro amplification techniques are used it is possible to incorporate a label, either immobilizable or detectable via the use of labelled mononucleoside triphosphates or labelled primers, into these amplification products, which thereafter will be used as the real nucleic acids A in the present invention. After appropriate preparation of the sample, at least one strand of the analyte A (or of the amplification products, which will act equally well as the nucleic acid A in the present invention), is made available by denaturation. Then nucleic acid analogues B, C and nucleic acid or analogue D, either of which may be labelled detectably or immobilizably, dependent upon the kind of label, if any, used in the nucleic acid A, is added to the reaction mixture. The components are incubated under conditions favouring the formation of the duplex structures and the triplex structure according to the invention. The complex may then be detected directly by various techniques that will allow separation of the complex from the single components, e.g. chromatography or electrophoresis, or the complex may be immobilized on a solid support. If immobilized, non-bound components and other constituents of the reaction mixture are separated from complex bound on the solid phase. Especially, excess detectably labelled nucleic acid or nucleic acid analogue should be removed from the complex. The bound complex is then detected, e.g. via a detectable label. The presence of the complex on the solid phase will be a measure for the presence of the original analyte nucleic acid A.

A preferred composition of matter, subject of this invention, contains a nucleic acid A having a sequence A1 and a sequence A2 adjacently connected, a first nucleic acid analogue B having a sequence B1 complementary to sequence A1 and a sequence B2 capable of participating in a triple helix structure containing a complementary nucleic acid or nucleic acid analogue D, and a second nucleic acid analogue C having a sequence C1, capable of participating in a triple helix structure containing said complementary nucleic acid or nucleic acid analogue D, and a sequence C2 complementary to sequence A2. The composition of matter is preferably in the form of a complex formed between said components, each complex containing one molecule of each component, B and C being bound to A via double helix formation, and to D via triple helix formation.

The nucleic acid or nucleic acid analogue D, contains a sequence which can participate in a triple helix structure also containing sequences B2 and C1 of the first and second nucleic acid analogues. This triplex is preferably made via a sequence D1. The nucleic acid or nucleic acid analogue D may contain further segments, for example a sequence D2. The complex formed from A, B, C and D, now called ABCD, is a preferred final product in the method for the determination or analysis of nucleic acid A. All specific embodiments and definitions as given in the above method apply to the composition of matter.

A further subject of the invention is a composition of matter containing a nucleic acid A having a sequence A1 and a sequence A2 adjacently connected, a first nucleic acid analogue B having a sequence B1 complementary to sequence A1 and a sequence B2 capable of participating in a triple helix structure containing a complementary nucleic acid or nucleic acid analogue, and a nucleic acid analogue C having a sequence C1 capable of participating in a triple helix structure containing said complementary nucleic acid or nucleic acid analogue and a sequence C2 complementary to sequence A2. The composition of matter is preferably in the form of a complex formed between said components A, B, and C, each complex containing one molecule of each component, B and C being bound to A via double helix formation. It has a preferred use as an intermediate product, formed during the determination of the nucleic acid A.

A further subject of the invention is the composition of matter containing a first nucleic acid analogue B having a sequence B1 and a sequence B2 capable of participating in a triple helix structure containing D, and a second nucleic acid analogue C having a sequence C1, capable of participating in a triple helix structure containing D, and a sequence C2. This composition of matter can be used as a multi component probe system for the determination of nucleic acid A, wherein sequences B1 and C2 are capable of binding to sequences A1 and A2 of the nucleic acid A. In the multi component complex, nucleic acid or nucleic acid analogue D, nucleic acid analogue B and nucleic acid analogue C are bound together via the triple helix structure formed by B2, C1, and segment DI of nucleic acid or nucleic acid analogue D.

A further subject of the invention is a reagent kit, for the determination of a nucleic acid A, containing in one or more containers the first nucleic acid analogue B, the second nucleic acid analogue C, and the nucleic acid or nucleic acid analogue D. The definitions above apply. This reagent kit can be used to store the components of the above mentioned method in a stable form, especially if all components are in separate containers. It might be advantageous, if two or more components are in a common container, especially the nucleic acid analogues B and C. Then less containers are necessary and the amount of pipetting steps, when performing the method, are reduced.

The following examples are given to examplify the invention and determine conditions for successful performance of the method:

General

The PNAs are synthesized according to WO 92/20702. If applicable, modifying groups are attached while the PNAs are still protected and on the solid phase. The PNAs have an amide function at the —COOH end because of the choice of solid support and the subsequent way to decouple the PNA from the solid phase. Thus, in this case we denote the C-end with —CONH$_2$. The amino end is denoted —H. DNA oligonucleotides are synthesized chemically on an automated synthesizer.

Analysis of conditions for triplex formation

In order to estimate the triplex forming ability of PNA probes B and C melting temperature (Tm) was measured at pH 5.0 and 9.5, since, at the higher pH, no Hoogsteen base pairing is possible. In total, 1 ml of a solution containing 0.1M phosphate buffer at the desired pH a solution of 9 µM PNA and 4.5 µM DNA was heated to 95° C. for 10 min., and allowed to cool slowly at 22° C. for 18 h. Subsequently, 2 ml 0.1M phosphate buffer was added, and the optical density was measured while ramping the temperature from 25° C. to 95° C. at 0.5° C./min. At pH 5.0 the Tm of segments B2 and C1, with a synthetic nucleic acid D was 62.6° C., whereas at pH 9.5 no Tm could be deduced. Such pH-dependency clearly indicates that Hoogsteen base pairing contributes significantly to the stability of the hybridization complex, and that triplex formation did not occur at pH 9.5. Also duplex formation was analysed at pH 5.0 and the Tm of segments B1 and C2, with a synthetic nucleic acid A, was 65.6° C. and 64.6° C. respectively.

Determination of a synthetic oligomer

Figure 3:
FIG. 3 shows all possible combinations of the components A,B,C and D and the complexes theoretically formed.
Figure 3:
Figure 3:
Figure 3:
Figure 3:
Figure 3:
Figure 3:
Figure 3:
Figure 3:
Figure 3:
Figure 3:

To estimate the complex formation, an experiment was setup using the components A, B, C, and D in the combinations described in FIG. 3. As the analyte nucleic acid A, 1 pmol $^{32}$P-labelled DNA oligonucleotide (SEQ.ID.NO. 1) was used. As the first nucleic acid analogue B and the second nucleic acid analogue C, 10 pmol of each of PNAs 195 and 286 Sequence were used. As D was used 1 pmol $^{32}$P-labelled DNA oligonucleotide (SEQ.ID.NO. 2).

SEQ.ID.NO. 1 5'-AAA-GAC-AAT-GGA-TTA-CCT-ATA-ACT-GTA-GAC-TCG-GCT-TGG-G-3'

PNA 195 H-Lys-GAG-TCT-ACA-GTT-Lys-TTC-TCC-TT-Lys-NH$_2$

PNA 286 H-Lys-TTC-CTC-TT-Lys-ATA-GGT-AAT-CCA-Lys-NH$_2$

SEQ.ID.NO. 2 5'-TAG-TTG-TGA-CGT-ACA-GAA-GGA-GAA

These components were incubated in 10 µL buffer containing:

100 mM NaCl; 10 mMNaH$_2$PO$_4$; 0.1 mM EDTA; pH 5.0

The samples were denatured at 95° C. for 5 minutes, followed by incubation at room temperature (RT) for 20 minutes. After addition of loading buffer (50% glycerol) samples were analysed on 20% PAGE.

Figure 2:
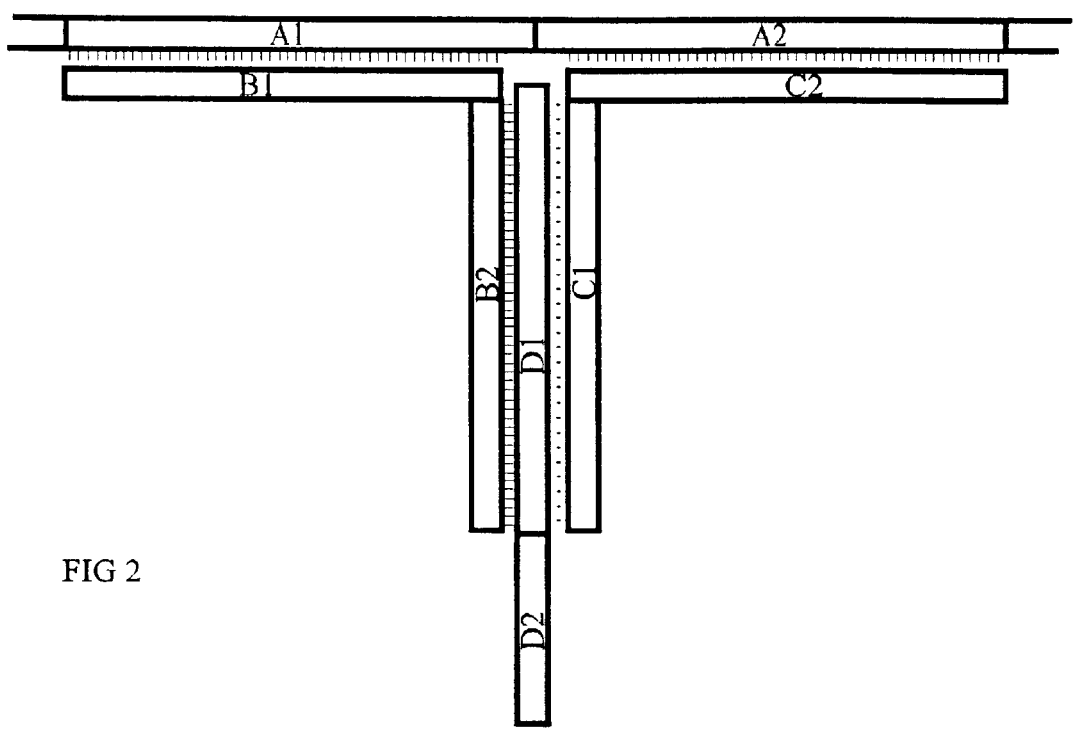
FIG. 2 shows schematically the arrangement of a nucleic acid A containing segments A1 and A2, a first nucleic acid analogue B containing segments B1 and B2 as well as a second nucleic acid analogue C containing segments C1 and C2 wherein the segments B2 and C1 are engaged in triplex formation with segment D1 of a nucleic acid or nucleic acid analogue D. Segment D2 may be used e.g. for detection or immobilization, or may be absent. This complex, in a composition of matter according to the invention, can be the result of a method for the determination of nucleic acid A.
Figure 4:
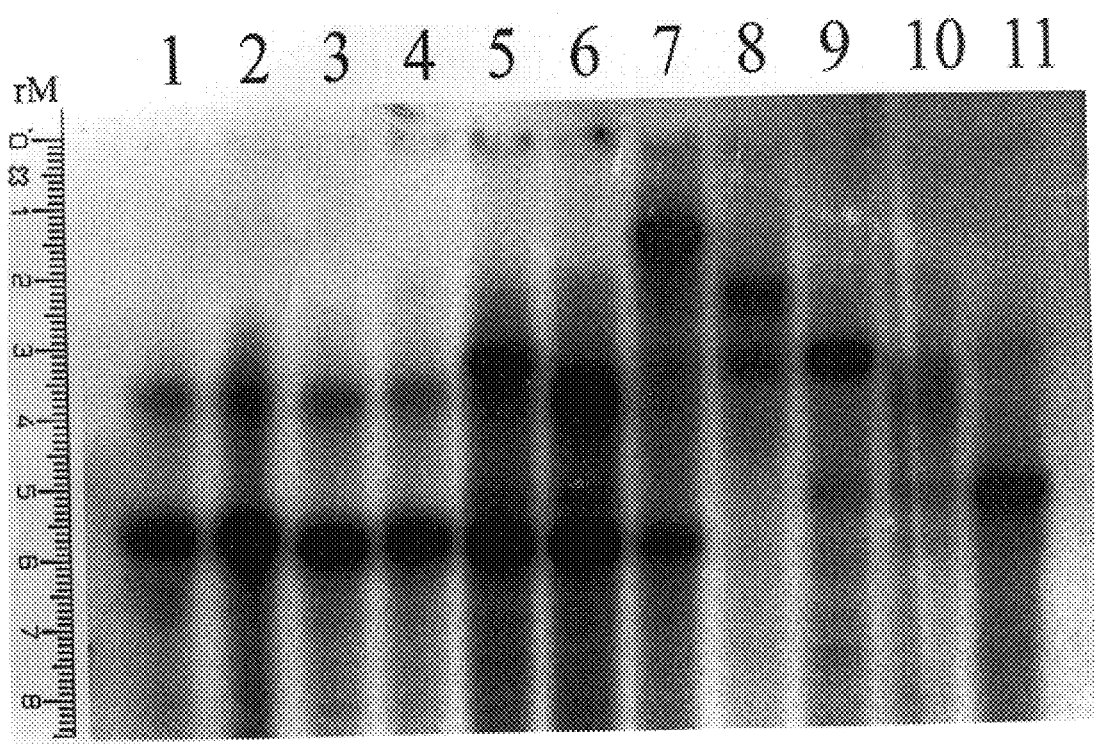
FIG. 4 shows an autoradiogram of the components, indicated in FIG. 3, run on PAGE.

FIG. 4 shows an autoradiogram of the gel, wherein it can be seen that the highest molecular weight compound is clearly the product depicted in FIG. 2. In FIG. 4 lanes 1–7 the DNA detection oligo (D), which is radiolabelled, can be seen as a strong band at 57 relative migration (rM) and as a fainter band at 37 rM (oligonucleotide synthesis by-product). The analyte DNA oligo (A), which is also radiolabelled, can be seen as a strong band in lane 11 at 50.5 rM, and is also visible in lanes 5–10. The PNA probes (B) and (C) do not form stable complexes (i.e. do not enter the gel) with D, neither alone (lanes 2 and 3) nor in combination (lane 4). They do, however, form complexes with the DNA analyte (A) and enter the gel to 31.5 rM (lane 5) and 36 rM (lane 6), respectively. These bands correspond to the bands in lanes 9 and 10 (analyte A plus one PNA, respectively) which indicates that the detection probe (D), present in lanes 5 and 6, does not form complexes with either of the hybrids (A/B or A/C) seen in lanes 9 and 10. Only when both PNA probes (B and C) are hybridised to the analyte (A) (as seen at 22 rM in lane 8) will they form a stable complex with the detection probe (D) as can be seen at 14 rM in lane 7. The formation of this complex containing all 4 components A B, C and D, therefore, is a specific demonstration of the analyte A.

We claim:

1. A method of detecting a nucleic acid A comprising a sequence A1 and an adjacent sequence A2, the method comprising:
   (a) providing a reaction mixture containing the nucleic acid A, in single-stranded form,
   a first nucleic acid analogue B, comprising a single-stranded sequence B1 which hybridizes to sequence A1, and a sequence B2 which does not directly base pair to nucleic acid A, and
   a second nucleic acid analogue C, comprising a sequence C1 which does not directly base pair to nucleic acid A, and a single-stranded sequence C2 which hybridizes to sequence A2,
   to form a complex ABC; and
   (b) determining the complex ABC, thereby detecting the nucleic acid A.

2. The method of claim 1, further comprising, in or after step (a), combining a single-stranded nucleic acid or nucleic acid analogue D with the reaction mixture or with the complex ABC, the nucleic acid or nucleic acid analogue D comprising a sequence D1 which forms a triple helix structure with the sequence B2 and the sequence C1, to form a complex ABCD; and wherein step (b) comprises determining the complex ABCD.

3. The method of claim 2, wherein the nucleic acid or nucleic acid analogue D further comprises a segment D2 which comprises a member selected from the group consisting of (1) a nucleobase sequence which is does not form a triple helix structure with the sequence B2 and the sequence C1, (2) a detectable label, and (3) an immobilizable label.

4. The method of claim 1, wherein the sequence A1 and the adjacent sequence A2 of the nucleic acid A are each at least 5 nucleobases long.

5. The method of claim 1, wherein the sequence A1 and the adjacent sequence A2 are separated by 0 to 5 nucleobases.

6. The method of claim 1, wherein the sequence A1 and the adjacent sequence A2 are separated by 0 or 1 nucleobase.

7. The method of claim 1, wherein the sequence A1 and the adjacent sequence A2 of the nucleic acid A are each independently 6 to 15 nucleobases long.

8. The method of claim 1, wherein the sequence B1 of the first nucleic acid analogue B and the sequence C2 of the second nucleic acid analogue C each consists of a peptide nucleic acid.

9. The method of claim 1, wherein the sequence B2 of the first nucleic acid analogue B and the sequence C1 of the second nucleic acid analogue C each independently has a length of 5 to 30 nucleobases.

10. The method of claim 1, wherein the sequence B2 of the first nucleic acid analogue B and the sequence C1 of the second nucleic acid analogue C each independently has a length of 6 to 20 nucleobases.

11. The method of claim 3, wherein the segment D2 comprises a nucleobase sequence which does not directly form a triple helix structure with the sequence B2 and the sequence C1, and said determining step comprises hybridizing to the segment D2 at least one probe having a label, and thereafter detecting the label.

12. The method of claim 3, wherein the segment D2 comprises a detectable label, and said determining step comprises detecting the detectable label.

13. The method of claim 3, wherein the segment D2 comprises a detectable label and the nucleic acid A further comprises an immobilizable label, wherein the method further comprises, before step (b), immobilizing the nucleic acid A to a support via the immobilizable label, and said determining step comprises detecting the immobilized detectable label.

14. The method of claim 3, wherein the segment D2 comprises an immobilizable label and the nucleic acid A further comprises a detectable label, wherein the method further comprises, before step (b), immobilizing the segment D2 to a support via the immobilizable label, and said determining step comprises detecting the immobilized detectable label.

15. The method of claim 3, wherein the segment D2 comprises a detectable label and one of the nucleic acid analogue B and the nucleic acid analogue C further comprises an immobilizable label, wherein the method further comprises, before step (b), immobilizing the nucleic acid analogue which comprises the immobilizable label to a support via the immobilizable label, and said determining step comprises detecting the immobilized detectable label.

16. The method of claim 3, wherein the segment D2 comprises an immobilizable label and one of the nucleic acid analogue B and the nucleic acid analogue C further comprises a detectable label, wherein the method further comprises, before step (b), immobilizing the segment D2 to a support via the immobilizable label, and said determining step comprises detecting the immobilized detectable label.

17. The method of claim 3, wherein one of the nucleic acid analogue B and the nucleic acid analogue C further comprises an immobilizable label and the other comprises a detectable label, wherein the method further comprises, before step (b), immobilizing the nucleic acid analogue which comprises the immobilizable label to a support via the immobilizable label, and said determining step comprises detecting the immobilized detectable label.

18. The method of claim 1, wherein, before step (b), complex ABC is separated from unreacted components of the reaction mixture.

19. A complex, comprising:
   a nucleic acid A, comprising (1) a sequence A1, and (2) an adjacent sequence A2;
   a first nucleic acid analogue B, comprising (1) a sequence B1 which is bound to the sequence A1 via double helix formation, and (2) a sequence B2 which is not bound to nucleic acid A; and a second nucleic acid analogue C, comprising (1) a sequence C1 which is not bound to nucleic acid A, and (2) a sequence C2 which is bound to the sequence A2 via double helix formation.

20. The complex of claim 19, further comprising a single-stranded nucleic acid or nucleic acid analogue D, comprising a single-stranded sequence D1 which forms a triple helix structure with the sequence B2 and the sequence C1.

21. The complex of claim 20, wherein the nucleic acid or nucleic acid analogue D further comprises a segment D2 which comprises a member selected from the group consisting of (1) a nucleobase sequence which does not form a triple helix structure with the sequence B2 and the sequence C1, (2) a detectable label and (3) an immobilizable label.

22. A complex, comprising:

a first nucleic acid analogue B, comprising a sequence B1 and a sequence B2;

a second nucleic acid analogue C, comprising a sequence C1 and a sequence C2; and a nucleic acid or nucleic acid analogue D, comprising a single-stranded sequence D1 which forms a triple helix structure with the sequence B2 and the sequence C1, wherein the sequence B1 and the sequence C2 each do not form a triple helix structure with the sequence D1.

23. A reagent kit for detecting a nucleic acid A comprising a sequence A1 and an adjacent sequence A2, the reagent kit comprising at least one container containing:

a first nucleic acid analogue B, comprising a single-stranded sequence B1 which hybridizes to sequence A1, and a sequence B2 which does not directly base pair to nucleic acid A;

a second nucleic acid analogue C, comprising a sequence C1 which does not directly base pair to nucleic acid A, and a sequence C2 which hybridizes to sequence A2; and a nucleic acid or nucleic acid analogue D, comprising a single-stranded sequence D1 which is configured to form a triple helix structure with the sequence B2 and the sequence C1.

24. The reagent kit of claim 23, wherein the nucleic acid or nucleic acid analogue D further comprises a segment D2 which comprises a member selected from the group consisting of (1) a nucleobase sequence which does not form a triple helix structure with the sequence B2 and the sequence C1, (2) a detectable label, and (3) an immobilizable label.

* * * * *